United States Patent [19]

Hofmann

[11] Patent Number: 4,524,079
[45] Date of Patent: Jun. 18, 1985

[54] DEACTIVATION OF MICROORGANISMS BY AN OSCILLATING MAGNETIC FIELD

[75] Inventor: Gunter A. Hofmann, San Diego, Calif.

[73] Assignee: Maxwell Laboratories, Inc., San Diego, Calif.

[21] Appl. No.: 550,894

[22] Filed: Nov. 10, 1983

[51] Int. Cl.³ .......................... A23L 3/00; A23L 3/26; A61L 2/02
[52] U.S. Cl. ..................................... 426/234; 422/22; 426/237; 426/241
[58] Field of Search ............... 426/234, 237, 238, 244, 426/240, 241; 422/22, 23

[56] References Cited

U.S. PATENT DOCUMENTS

| | | |
|---|---|---|
| 824,320 | 6/1906 | Weitzmann . |
| 1,044,201 | 11/1912 | Lincoln . |
| 1,063,170 | 5/1913 | Lincoln . |
| 1,162,213 | 11/1915 | Bloom . |
| 1,863,222 | 6/1932 | Hoermann . |
| 3,494,723 | 2/1970 | Gray ........................................ 21/54 |
| 3,809,845 | 5/1974 | Stenstrom ........................ 219/10.55 |
| 3,876,373 | 4/1975 | Glyptis ............................... 21/54 R |
| 4,042,325 | 8/1977 | Tensmeyer ........................ 21/54 R |
| 4,327,180 | 4/1982 | Chen .................................. 435/173 |

FOREIGN PATENT DOCUMENTS

| | | | |
|---|---|---|---|
| 110109 | 4/1940 | Australia .............................. 426/237 |
| 2253686 | 7/1974 | Fed. Rep. of Germany ........ 422/22 |
| 2300677 | 7/1974 | Fed. Rep. of Germany ........ 422/22 |
| 390131 | 6/1931 | United Kingdom ................. 426/237 |
| 706443 | 12/1979 | U.S.S.R. ............................... 426/238 |
| 716556 | 2/1980 | U.S.S.R. ............................... 422/22 |

Primary Examiner—Steven Weinstein
Attorney, Agent, or Firm—Fitch, Even, Tabin & Flannery

[57] ABSTRACT

Material having relatively high electrical resistivity, such as food products and containers, is disposed within a magnetic coil and subjected to one or more pulses of an oscillating magnetic field having an intensity of between about 2 and about 100 Tesla and a frequency of between about 5 and about 500 kHz. A single pulse of the magnetic field generally decreases the microorganism population by at least about two orders of magnitude, and substantially complete sterility is more closely approached by subjecting the material to additional pulses.

8 Claims, 1 Drawing Figure

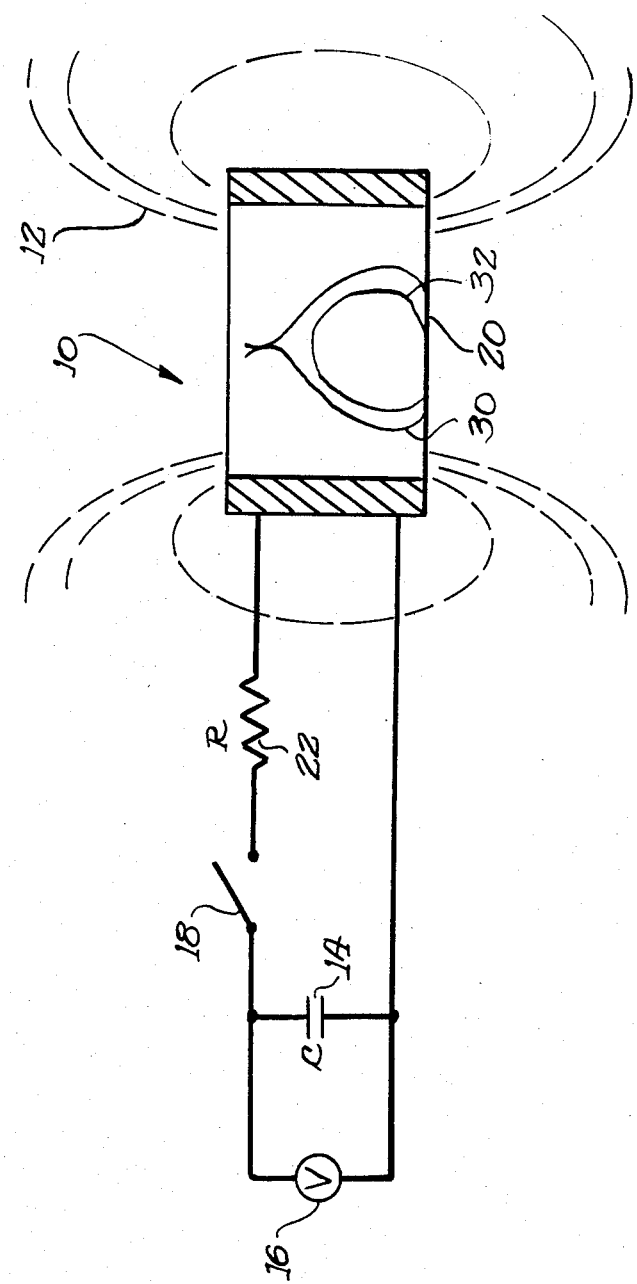

DEACTIVATION OF MICROORGANISMS BY AN OSCILLATING MAGNETIC FIELD

The present invention relates to a method of deactivating microorganisms and more particularly destroying microorganisms in non-electrically conductive material, such as food and food product containers.

BACKGROUND OF THE INVENTION

Although many microorganisms have been put to uses that are quite helpful to man, man has long tried to destroy other microorganisms or microorganisms in environments where their presence is considered undesirable or harmful.

In response to the need to preserve food, man has devised a variety of processes which either kill microorganisms or deny microorganisms a suitable environment for continued growth in the food and/or in containers for preserving food products. Food preservation processes used since prehistoric times include heating (cooking), smoking, salting and drying. In modern times a number of new technologies have been used in attempts to find better ways to preserve food. Some modern methods, such as microwave cooking, are merely new ways to effect an old process, i.e., heating. Other recently developed sterilization methods destroy microorganisms in a novel manner. U.S. Pat. No. 3,876,373 describes sterilizing matter by exposing the material to a plasma. U.S. Pat. No. 1,863,222 describes sterilizing food or other products by placing the material in the conductive pathway of a high frequency electrical circuit. Other methods of preserving food or the like include subjecting them to various types of radiation, such as ultraviolet light.

Most methods of processing food to inactivate microorganisms substantially alter the nature of the food. In many cases, the effect of the process on the food may prove to be quite desirable. In other cases, particularly with some of the newer technologies, the processes impart characteristics to the foods that are considered by many to be undesirable.

There are many applications where it would be desirable to preserve food without effecting any change in the food except destruction of the microorganisms which cause its eventual spoilage. For example, it would be desirable to pasteurize milk without the flavor changes attendant ordinary thermal pasteurization or the even less desirable flavor changes attendant the recently introduced process known as "ultrapasteurization". Likewise it would be desirable to prevent spoilage in meat prior to cooking for longer periods of time without freezing. In other food products, such as cheese or beer, microorganisms play an inherent role in their production; however, after a certain stage, continued growth of microorganisms is detrimental to the product. Thus, a cheese should be eaten at a certain ripeness, whereas beer is frequently pasteurized for long term bottling. The shelf life and/or palatability of such food products should be improved if the microorganism used to produce these products could be inactivated without otherwise altering the product.

Magnetic fields have been used previously in conjunction with certain food processing steps. For example, in U.S. Pat. No. 4,042,325, a magnetic field is used to maintain a laser-generated plasma. Of course, microwave cooking subjects food to a magnetic field; however, as mentioned above, the induced thermal effect kills microorganisms while substantially altering the character of the food.

SUMMARY OF THE INVENTION

Herein, it is discovered that moderate frequency, high intensity magnetic fields can be used to destroy or otherwise inactivate microorganisms within a generally non-electrically conductive environment. Destruction of microorganisms within food when subjected to an oscillating magnetic field is accomplished within very short time periods during which no significant temperature rise is detectable in the food. The food is sterilized without any detectable change in its character, without a plasma being produced and without the addition of chemicals.

Material that has a very low electrical conductivity, such as food, is subjected to a high intensity, moderate frequency oscillating magnetic field for a very short period of time, during which exposure the microorganisms are either destroyed or reproductively inactivated. During the short period of time that the material is subjected to the oscillating magnetic field, heating of the material is minimal, and except for destruction of the microorganisms, the material is substantially unaltered. In particular, the microorganism count in food products is drastically reduced, yet the taste of the food is unaltered.

BRIEF DESCRIPTION OF THE DRAWING

The FIGURE is a diagrammatic illustration of a food product disposed within an electromagnetic coil and a simplified circuit associated with the coil for generating an oscillating magnetic field within the coil.

DETAILED DESCRIPTION OF A PREFERRED EMBODIMENT

In accordance with the present invention, material having a low electrical conductivity is subjected to a high intensity, moderate frequency oscillating magnetic field for a very short period of time, killing or inactivating a major portion of the microorganisms within or upon the material to achieve substantial sterilization without detectably altering the material itself. Destruction or deactivation of major portions of the microorganisms present is referred to herein as "sterilization" although not all the microorganisms present are destroyed as would be required to make the product technically or completely "sterile". By microorganisms is meant those organisms usually so classified, such as fungi, molds, spores, viruses, protozoa and algae; however, with respect to the treatment of food or food product containers, particular emphasis is placed upon bacteria, spores and molds.

It is found that subjecting a food product to a single oscillating magnetic field decay period at frequencies above about 5 kHz and intensities above about 5 Tesla will reduce the number of microorganisms in the food product by about two orders of magnitude. Substantially complete sterilization can be effected by subjecting the product to additional pulses of the magnetic field. Because of the short duration of each pulse, even up to about 100 such pulses do not significantly raise the temperature of the product itself, and a food product can be substantially sterilized without raising its temperature, either at the surface or internally, more than about 5° C. and typically no more than about 2° C.

Illustrated diagrammatically in the FIGURE is an electromagnetic coil 10 and associated circuitry which produce magnetic pulses of moderate frequency and high intensity. Apparatus of the general type illustrated is currently used for metal forming. An example of suitable apparatus is that sold under the trademark Magneform by Maxwell Laboratories, Inc. A metallic object placed within the coil and exposed to intense magnetic pulses, represented by flux lines 12, is subjected to strong radial stresses which radially deform the object. The surprising discovery was made that by placing nonconductive material within the magnetic coil and subjecting the material to a moderate frequency, high intensity magnetic field, a very substantial proportion of the microorganisms carried thereon or therein are inactivated.

The magnetic field in the coil is produced upon discharge of a capacitor 14. The capacitor is charged from a source 16, and when a switch 18 is closed, completing the circuit that includes the capacitor and the coil, an oscillating current is generated between the plates of the capacitor. The oscillating current in turn generates an oscillating magnetic field which is concentrated within the region 20 bounded by the coil. The frequency of the oscillating field is determined by the capacitance of the capacitor and the resistance and inductance of the circuit, which are primarily determined by a resistor 22 and the inductance of the coil 10. Immediately subsequent to closing the switch, an intense magnetic field is produced by current flowing in one direction. As the current changes direction, the magnetic field changes polarity. The oscillating current and, hence, the oscillating magnetic field rapidly deteriorates, with the field intensity after about ten oscillations dropping to a few percent of the original intensity. Herein, magnetic field intensities refer to the intensity of the initial peaks.

The invention is applicable to killing microorganisms in a wide variety of materials, the major requirement being that the material have a low electrical conductivity, or inversely, a high electrical resistivity, so that the interior regions of the material are not excessively shielded from the coil-generated magnetic field by induced eddy currents. For purposes of this invention, the material should have a resistivity at least above about 10 ohms-cm and preferably at least above about 25 ohms-cm. Almost any conceivable food product, whether liquid or solid, will have a resistivity within the preferred range; for example, orange juice has a resistivity of about 30 ohms-cm, a resistivity which is considered low relative to most other food products. Similarly, most biological specimens have electrical resistivities within the preferred range, and thus the method of the invention is particularly suitable for processing a biological specimen by killing or inactivating the microorganisms and thereby preserve the specimen in its original condition until laboratory tests can be performed. Many plastic materials can be similarly sterilized, making the method of the invention particularly suitable for sterilizing plasticware for medical or related purposes.

Furthermore, materials such as cardboard or plastic that are frequently used to form food packages have resistivities within the required range. Food products may be packaged in their non-conductive containers and sterilized within such container. A significant limitation to sterilizing prepackaged food, is that metal containers, including foil wrap, are unsuitable for purposes of the invention because metal will shield the product from the effect of the magnetic field and because the metal will be deformed by the high intensity magnetic field.

The material that is to be sterilized requires no special preparation prior to subjecting it to the magnetic field. No chemical additives are required. No special atmosphere is required as no plasma is generated. The method will sterilize the immediate environment, whether liquid or gaseous, and the material is ordinarily sterilized at atmospheric pressure and at temperatures which contribute to the stability of the product.

Typically, the product is sterilized at room temperature, but it may be sterilized at temperatures which range from below 0° C. to 50° C. or above. In many cases, however, the material is presealed in a suitable container so that the sterilization is not undone by subsequently exposing the product to contamination. Represented in the FIGURE is a food product 32 sealed within a plastic bag 30 and centered within the magnetic coil 10.

The intensity of the magnetic field that is used may be as low as about 2 Tesla and about as high as about 100 Tesla, and preferably the field intensity is between about 5 and about 50 Tesla. The actual intensity of the magnetic field used depends on the properties of the material being sterilized, including the resistivity of the material and its thickness, with higher intensities being used for material of lower resistivities and greater thickness. There is no direct relationship that is currently worked out relating intensities to types of materials, and sufficient destruction of microorganisms may be effected by adjusting other parameters, such as exposure time, which in the case of a Magneform, is a function of the number of pulses.

Microorganism destruction is most effective when oscillating fields are used having frequencies in the range of from about 5 to about 500 kHz. This frequency range is described herein as a moderate frequency range. In comparison, microwave frequencies are several orders of magnitude higher, i.e., in the megaherz/gigaherz range. Frequencies above 500 kHz are less effective in inactivating microorganisms by magnetic oscillation and rather tend to heat the material.

Total exposure time of the product to the magnetic field is minimal, ranging from about 25 microseconds up to about 10 milliseconds. With reference to the above-described apparatus, exposure time can be considered the number of pulses multiplied by the duration of each pulse. Herein pulse duration is considered to be 10 oscillations, after which the substantially decayed field has a negligible effect. A single pulse generally decreases the population of a microorganism by about two orders of magnitude; however, additional pulses may be used to effect a greater degree of sterilization, and, typically, food products are subjected to between about 10 pulses and about 100 pulses.

The major constraint on the intensity of the field and the number of pulses is that it may be desirable that the material should not be significantly heated. Heating is not generally a concern when food product containers are being treated, and they will normally be subjected to at least about 5 pulses. Any cooking of food products is to be avoided, and it is considered desirable that the product not be heated more than about 5° C., and preferably not more than 2° C., either at the surface or internally, by the magnetic sterilization procedure. Most food products can be subjected to 100 pulses at about 50 Telsa without being heated more than about 5° C. If it appears to be desirable to subject the food to additional pulses, the product may be pre-chilled, thereby avoiding heating the material to where the product would be affected. Generally, significant additional sterility is not felt to result from subjecting the material to more than about 100 pulses.

The magnetic field does not significantly affect the properties of low electrical conductivity products. The taste of food subjected to magnetic fields according to invention is not altered so as to be detected by experienced tasters. Likewise, the molecular structure of low-conductivity containers does not appear to be affected by the magnetic field.

The reason that microorganisms are killed or rendered reproductively inactive has not yet been determined. It is suggested that the oscillating magnetic field might couple energy into magneto-active parts of critical large molecules, such as DNA, in the microorganisms. Within the intensity range of 5-50 Tesla, the amount of energy per oscillation coupled to one dipole is $10^{-2}$ to $10^{-3}$ ev. With several oscillations and a collective assembly of dipoles, enough local activation may result in destruction of a covalent bond, which typically has an energy in the vicinity of about 1 ev. It is expected that similar events would occur in the material being sterilized; however, whereas random destruction of a very minimal number of bonds in the inanimate material would be undetectable and not affect the macro-characteristics of the material, breakage of certain bonds in critical large molecules in a microorganism might kill the microorganism or render it reproductively inactive.

Whether the microorganisms are actually killed or only rendered inactive is uncertain. The standard plate count method used to demonstrate enhanced sterility of the material does not distinguish between those microorganisms immediately killed and those that do not reproduce. It is felt that while some of the microorganisms are killed outright, the major reduction in microorganism count may be a result of weakening of microorganisms so that they do not reproduce. Certain cultures of surviving bacterial colonies are markedly different from healthy bacterial colonies, indicating that the magnetic field traumatizes the genetic material of the cell, and presumably, in most cases, this structure is so damaged as to render the cell reproductively non-viable.

An additional advantage of the magnetic sterilization process is that it is generally very safe to perform. The high intensity magnetic field exists only within the coil and immediately thereabout. Within a very short distance from the coil, the magnetic field drops off dramatically. For example, whereas the field generated by a coil may have an intensity of 7 Tesla interior of the coil, within about 2 meters exterior of the coil, the intensity drops off to about $7 \times 10^{-5}$ Tesla, i.e., comparable to the magnetic field of the earth. Thus, providing that the operator is positioned a reasonable distance from the activated coil, there is substantially no likelihood of cells in the tissues of the operator being affected in a manner similar to the microorganism cells, and the process may be operated without special shielding. One exception to this is that, as is the case with microwave apparatus, it should not be operated in the presence of persons wearing certain prosthetic devices, such as pacemakers.

The invention will now be described more fully by way of specific examples:

Example 1

A sample of pasteurized milk is repasteurized by heating it to 90° C. and immediately transferred to a sterile plastic bag. The milk is inoculated with *Streptococcus thermophilus* at a concentration of 25,000 bacteria/cm$^3$. The bag is sealed and shaken vigorously to assure diffusion of the inoculum throughout the sample.

The temperature of the milk is measured to be 23° C., and the bag of milk is disposed centrally in a 20 k joule Magneform, 7000 series coil. The milk is subjected to 1 pulse of a 12 Tesla, 6 kHz, oscillating magnetic field. A portion of the milk is withdrawn from the bag, and its temperature is measured and found to be 24° C. An aliquot of the milk is plated on a standard plate. The colony count of the plate shows a concentration of about 970 *Streptococcus thermophilus* per cm$^3$.

A panel of food processing experts cannot distinguish the magnetically sterilized milk from a sample of milk that is contemporaneously repasteurized.

This experiment demonstrates that a substantial proportion of microorganisms in a food sample can be killed by subjecting the food sample to a high intensity, moderate frequency, oscillating magnetic field. The process does not significantly affect the temperature of the food product and does not alter the taste of the food.

Example 2

A waxed cardboard container containing 350 g of plain 4% fat yogurt is opened, inoculated with Saccharomyces at a concentration of 3,500 bacteria/cm$^3$ and stirred thoroughly. As a control, similar containers of non-inoculated yogurt are contemporaneously stirred. The covers are replaced, and all samples are maintained at 4° C.

The container full of inoculated yogurt is placed centrally within the coil described above and subjected to 10 pulses of a 40 Tesla, 416 kHz, oscillating magnetic field. Then thermal probes are inserted into the yogurt at a central location and at a location near its upper surface, and both probes register a reading of 6° C. after magnetic field exposure. A sample of the yogurt is plated on standard plates, and a count of the cultures reveals a concentration of only about 25 Saccharomyces bacteria per cm$^3$ of yogurt.

A taste panel of experienced tasters can detect no difference between the inoculated and magnetically sterilized sample and the stirred control samples.

Example 3

Reconstituted orange juice is inoculated with Saccharomyces at a concentration of 25,000 bacteria per cm$^3$. The orange juice, maintained at 20° C., is placed in a plastic container, and the container is placed centrally within the above-described coil. The orange juice is subjected to 1 pulse of a 40 Tesla, 416 kHz, oscillating magnetic field. The temperature of the orange juice is measured to be 21° C. A sample of the orange juice is plated on standard plates, and a culture count shows a concentration of only about 6 bacteria per cm$^3$.

A panel of experienced tasters cannot tell the difference between the orange juice subjected to the magnetic field and a control orange juice sample.

Example 4

A prepackaged dough product sold under the trademark "Brown'N Serve Rolls" is finely chopped in a food processor, and the finely chopped product is thoroughly mixed with mold spores to give a concentration of 3000 spores/cm³. The chopped rolls are placed in a plastic bag which was centered in the above-described coil where it was subjected to 1 pulse of a 7.5 Tesla, 8.5 kHz, oscillating magnetic field. A sample of the chopped rolls is plated on standard plates, and a culture count shows a mold spore concentration of only about 1 spore per cm³.

Because a taste test cannot fairly be performed on the chopped product, a roll is placed in a plastic bag and subjected to similar magnetic field treatment. Then the roll is browned according to package directions alongside a roll from the same package. A panel of experienced tasters cannot tell the difference between the roll subjected to the magnetic field and the co-packaged roll.

Although the invention has been described in terms of a preferred embodiment, modifications obvious to one with ordinary skill in the art may be made without departing from the scope of the invention. For example, although sterilization is effected in the absence of more conventional sterilization procedures, such as heating or exposure to chemicals, it is understood that the magnetic sterilization practiced in accordance with the present invention may be used in conjunction with other sterilization procedures.

Various features of the invention are set forth in the following claims:

What is claimed is:

1. A method of deactivating microorganisms present in material having an electrical resistivity of at least about 10 ohms-cm which method comprises,
    subjecting said material to at least one pulse of a pulsed, decaying, oscillating magnetic field having an intensity of between about 2 and about 100 Tesla and a frequency of between about 5 and about 500 kHz.

2. A method according to claim 1 wherein said magnetic field has an intensity of between about 5 and about 50 Tesla.

3. A method according to claim 1 wherein said material is exposed to between about 1 about 100 pulses.

4. A method according to claim 3 wherein the number of pulses does not heat the material more than about 5° C.

5. A method according to claim 3 wherein said material is exposed to at least about 10 pulses.

6. A method according to claim 1 wherein said material has an electrical resistivity of at least about 25 ohms-cm.

7. A method according to claim 1 wherein the material treated is a food product packaged within a closed container.

8. A method of sterilizing a food product container having an electrical resistivity of at least about 25 ohms-cm comprising subjecting said container to at least about 5 pulses of a pulsed, decaying, oscillating magnetic field having an intensity of between 2 and 100 Telsa and a frequency of between about 5 and about 500 kHz.

* * * * *